United States Patent
Stahmann et al.

(10) Patent No.: US 7,894,914 B2
(45) Date of Patent: *Feb. 22, 2011

(54) MEDICAL DEVICE ELECTRODES INCLUDING NANOSTRUCTURES

(75) Inventors: Jeffrey E. Stahmann, Ramsey, MN (US); Rodney W. Salo, Fridley, MN (US); Jihong Qu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 98 days.

This patent is subject to a terminal disclaimer.

(21) Appl. No.: 11/846,246

(22) Filed: Aug. 28, 2007

(65) Prior Publication Data

US 2009/0062895 A1 Mar. 5, 2009

(51) Int. Cl.
*A61N 1/05* (2006.01)
(52) U.S. Cl. .......... 607/119; 600/372; 600/373; 600/374; 607/116; 607/122; 977/931
(58) Field of Classification Search .......... 600/372–374, 600/395; 607/116, 119, 122, 123, 126, 127, 607/3, 53–54, 120; 977/904, 931
See application file for complete search history.

(56) References Cited

U.S. PATENT DOCUMENTS

| 3,835,864 | A | 9/1974 | Rasor et al. |
|---|---|---|---|
| 4,256,115 | A | 3/1981 | Bilitch |
| 7,079,903 | B2 | 7/2006 | O'Brien |
| 7,129,554 | B2 | 10/2006 | Lieber et al. |
| 7,126,308 | B2 | 1/2007 | O'Brien et al. |
| 7,194,315 | B1 | 3/2007 | Platt et al. |
| 7,582,222 | B2 | 9/2009 | Martin et al. |
| 2003/0171257 | A1 | 9/2003 | Stirbl et al. |
| 2003/0229393 | A1 | 12/2003 | Kutryk et al. |
| 2004/0106951 | A1 | 6/2004 | Edman et al. |
| 2004/0111141 | A1 | 6/2004 | Brabec et al. |

(Continued)

FOREIGN PATENT DOCUMENTS

EP 1424095 6/2004

(Continued)

OTHER PUBLICATIONS

T.D. Barbara Neguyen-Vu, Hua Chen, Alan M. Cassell, Fussel J. Andrews, M. Meyyappan, Jun Li, Vertically Aligned Carbon Nanofiber Architecture as a Multifunctional 3-D Neural Electrical Interface, 2007, IEEE Transactions on Biomedical Engineering, vol. 54, No. 6, 1121-1128.*

(Continued)

*Primary Examiner*—Carl H Layno
*Assistant Examiner*—Jennifer Stewart
(74) *Attorney, Agent, or Firm*—Faegre & Benson LLP

(57) ABSTRACT

Electrodes for tissue stimulation and sensing can comprise a support with nanostructures disposed on the support. Pairs of the electrodes can be placed in close proximity to one another. When electrical energy is supplied to the electrodes, an electrical field (and possibly an electrical current) can be established between the nanostructures on the electrodes. The nanostructures may have cells disposed thereon, for example myocardial cells, myocardial progenitor cells, neural cells and/or stem cells. In addition, the electrodes can be arranged in arrays.

24 Claims, 6 Drawing Sheets

U.S. PATENT DOCUMENTS

| | | | |
|---|---|---|---|
| 2004/0199235 A1 | 10/2004 | Younis | |
| 2004/0202603 A1 | 10/2004 | Fischer et al. | |
| 2005/0038498 A1* | 2/2005 | Dubrow et al. | 623/1.15 |
| 2005/0101020 A1 | 5/2005 | Salem et al. | |
| 2005/0203604 A1 | 9/2005 | Brabec et al. | |
| 2005/0221072 A1 | 10/2005 | Dubrow et al. | |
| 2005/0246002 A1* | 11/2005 | Martinez | 607/116 |
| 2006/0136027 A1 | 6/2006 | Westlund et al. | |
| 2006/0239891 A1 | 10/2006 | Niu et al. | |
| 2007/0060815 A1 | 3/2007 | Martin et al. | |
| 2007/0073130 A1 | 3/2007 | Finch et al. | |
| 2007/0123766 A1* | 5/2007 | Whalen et al. | 600/395 |
| 2007/0138007 A1 | 6/2007 | Yemini et al. | |
| 2008/0255439 A1* | 10/2008 | Tang et al. | 600/373 |
| 2008/0319496 A1* | 12/2008 | Zhu et al. | 607/5 |
| 2009/0062894 A1 | 3/2009 | Stahmann et al. | |

FOREIGN PATENT DOCUMENTS

| | | |
|---|---|---|
| EP | 1454651 | 9/2004 |
| WO | 2004030706 | 4/2004 |
| WO | 2004/041996 | 5/2004 |
| WO | 2005046470 | 5/2005 |
| WO | 2005107849 | 11/2005 |
| WO | 2006131912 | 12/2006 |
| WO | 2007028003 A | 3/2007 |

OTHER PUBLICATIONS

J. Li and R.J. Andrews, Trimodal nanoelectrode array for precise deep brain stimulation: prospects of a new technology based on carbon nanofiber arrays, 2007, Acta Neurochir Supplemental, 97(2),537-545.*

Charles Merritt and Brian Justus, Fabrication of Mircoelectrode Arrays Having High-Aspect-Ratio,2003, Chem. Mater, 15, 2520-2526.*

Levashov et al., "Nanoparticle dispersion-strengthened coatings and electrode materials for electrospark deposition," Thin Solid Firms 515:1161-1165, 2006.

International Search Report and Written Opinion of international application No. PCT/US2008/072811, mailed Nov. 25, 2008, 18 pp.

Andriotis et al., "Rectification Properties of Carbon Nanotube 'Y-Junctions,'" The American Physical Society, Physical Review Letters, Aug. 6, 2001, vol. 87, No. 6, pp. 066802-1-4.

Ding et al., "Molecular Characterization of the Cytotoxic Mechanism of Multiwall Carbon Nanotubes and Nano-Onions on Human Skin Fibroblast," Americal Chemical Society, Nano Letter, 2005, vol. 5, No. 12, pp. 2448-2464.

Mase et al., "Histopathological Study of Tissue Reaction to Pacemaker Electrodes Implanted in the Endocardium," Nippon Medical School, 2005; 72(1), pp. 52-69.

Kim, et al., "Modulation of Adhesion and Growth of Cardiac Myocytes by Surface Nanotopography," Proceeding of the 2005 IEEE, Shanghai, China, Sep. 1-4, 2005, pp. 4091-4094.

Liopo et al., "Biocompatibility of Native and Functionalized Single-Walled Carbon Nanotubes for Neuronal Interface," Journal of Nanoscience and Nanotechnology, 2006, vol. 6, pp. 1365-1374.

Website, "Drug Delivery Down the Tubes," NMR knowledge Base—The NMR Resource, Oct. 1, 2005, http://www.spectroscopynow.com.

Website, "Nanotubes Used for First Time to Send Signals to Nerve Cells," Medical News Today, May 12, 2006, http://www.medicalnewstoday.com Website, "CSC Scientists Discover Ways to Build Chips from the Atom Up," CSC-Features, 2003, http://www.csc.com/features/2003/149.shtml.

Website, "Nanotubes to Send Signals to Nerve Cells," Archives of Research News Blog from Medicineworld.org, May/Jun. 2006, http://medicineworld.org/news/news-archives/research-news/June 15-2006.html.

Shin et al., "Contractile Cardiac Grafts Using a Novel Nanofibrous Mesh," ScienceDirect-Biomaterials, Aug. 2004, vol. 25, Issue 17, pp. 3717-3723.

International Search Report and Written Opinion of International Application No. PCT/US2008/072807, mailed Mar. 10, 2009, 14 pages.

Rustom et al, "Nanotubular Highways for Intercellular Organelle Transport," Science, vol. 303, pp. 1007-1010, Feb. 13, 2004, www.sciencemage.org.

* cited by examiner

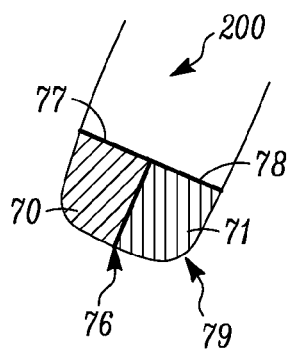
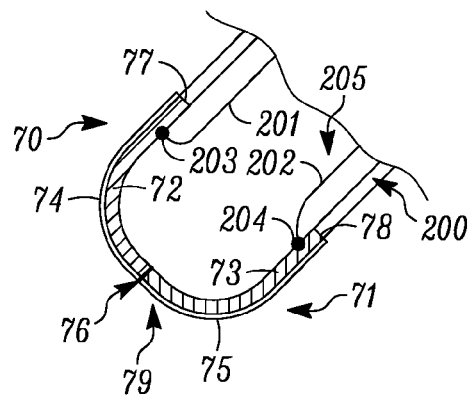
FIG. 3A    FIG. 3B
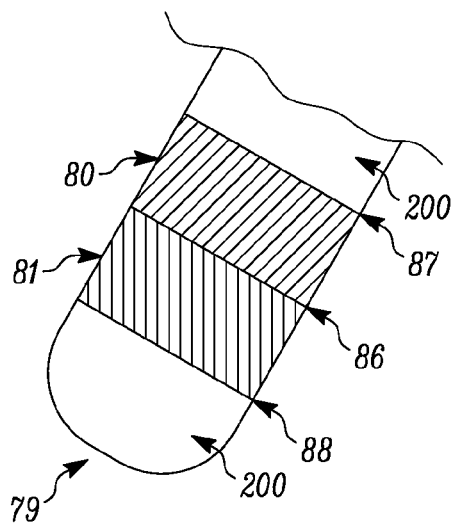
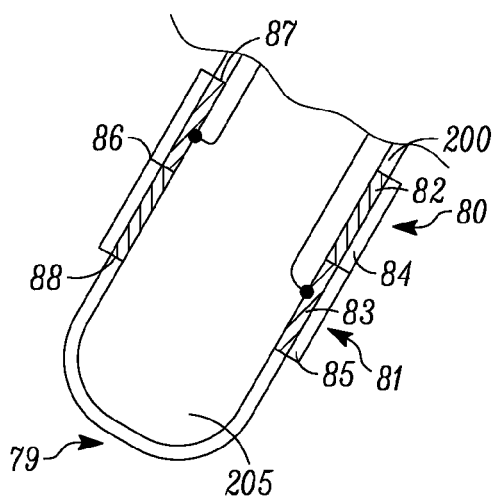
FIG. 4A    FIG. 4B

MEDICAL DEVICE ELECTRODES INCLUDING NANOSTRUCTURES

CROSS-REFERENCE TO RELATED APPLICATION

This application is related to application Ser. No. 11/846,280, entitled "Medical Device Electrode Having Cells Disposed on Nanostructures", which is filed on an even date herewith and is incorporated by reference in its entirety.

TECHNICAL FIELD

The present invention relates to implantable medical devices for stimulating body tissues and/or sensing physiological attributes. More specifically, the invention relates to electrode configurations in medical devices including nanostructures.

BACKGROUND

Various physiological functions can be managed and/or monitored using implantable devices. Implantable devices can provide stimulating and/or sensing functionality to assist with a patient's health care. For example, implantable devices have been used in association with cardiac rhythm management, which can include cardiac pacing, cardiac defibrillation, and/or cardiac therapy, among other procedures. To facilitate these procedures, implantable devices can be configured for stimulating cardiac tissues and/or sensing the function of cardiac tissues. There exists a need for alternative devices and methods for stimulating and/or sensing cardiac function.

SUMMARY

In one embodiment of the invention, a medical device comprises a device body with an array of electrodes disposed thereon. The array includes a plurality of first electrodes and a plurality of second electrodes. At least one of the first electrodes is electrically connected to a first electrical connection and at least one of the second electrodes is electrically connected to a second electrical connection. The first and second electrodes comprise nanostructures, and the nanostructures of the first electrodes are at least partially encapsulated within living cells.

In another embodiment of the invention, a bipolar medical electrical lead comprises a first electrode electrically connected to a first electrical connection and a second electrode electrically connected to a second electrical connection. The first and second electrodes comprise first and second supports with first and second nanostructure coatings disposed on the first and second supports, respectively. The nanostructure coatings of the first and second electrodes are spaced apart from one another such that at least one of the first nanostructures of the first nanostructure coating and at least one of the second nanostructures of the second nanostructure coating are spaced less than approximately 45 μm from one another.

In yet another embodiment, a leadless medical electrical device has a first electrode with a first support and a second electrode with a second support. The first support has a first nanostructure coating disposed thereon and the second support has a second nanostructure coating disposed thereon.

While multiple embodiments are disclosed, still other embodiments of the present invention will become apparent to those skilled in the art from the following description, which shows and describes illustrative embodiments of the invention. Accordingly, the drawings and detailed description are to be regarded as illustrative in nature and not restrictive.

BRIEF DESCRIPTION OF THE DRAWINGS

FIG. 3A shows a perspective view of a pair of electrodes according to embodiments of the present invention;

FIG. 3B shows a cross-sectional view of the embodiments of FIG. 3A;

FIG. 4A shows a perspective view of a pair of electrodes according to embodiments of the present invention;

FIG. 4B shows a cross-section view of the embodiments of FIG. 4A;

Figure 1:
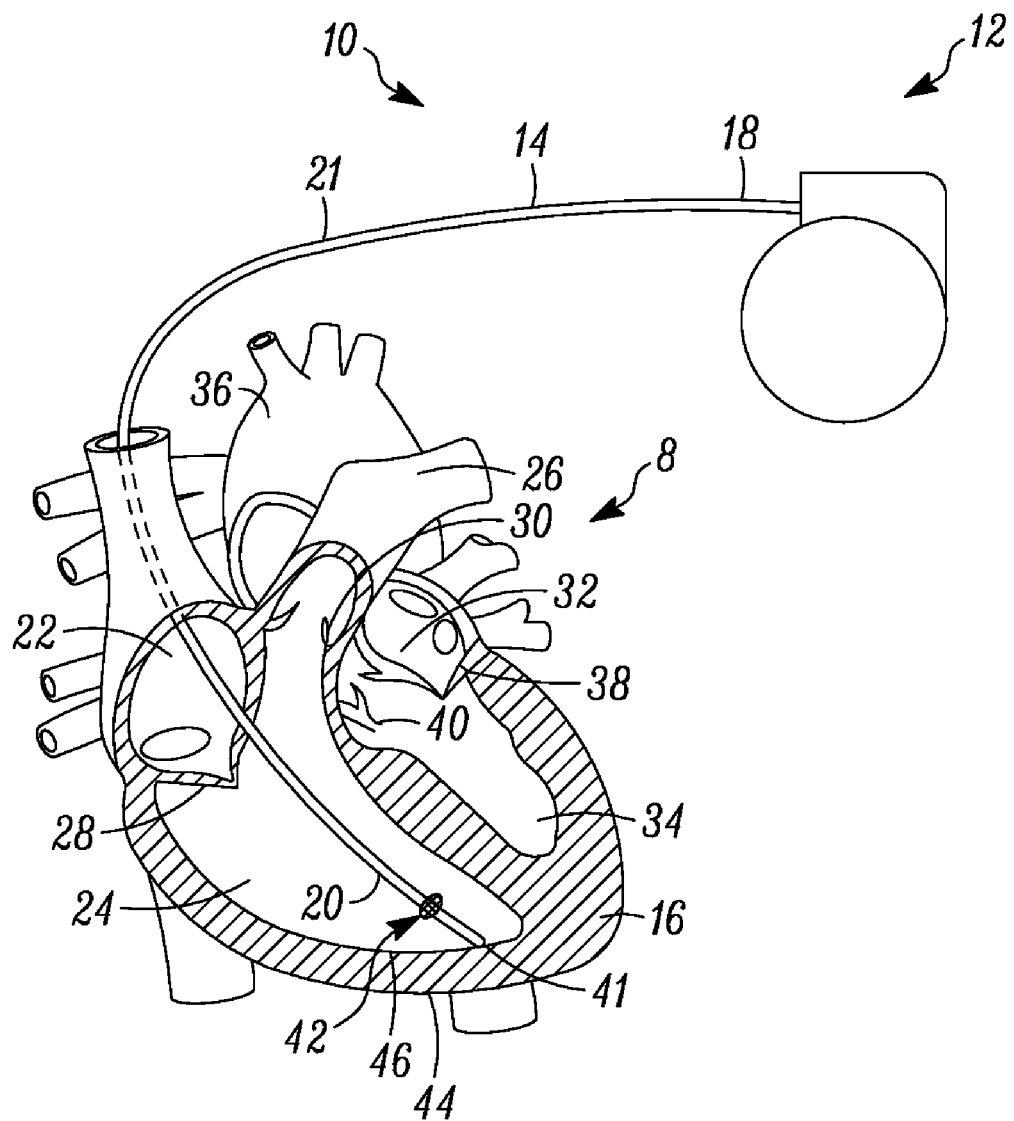
FIG. 1 shows an exemplary lead-based implantable medical device according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a combined cutaway view of a human heart 8 and a perspective view of an exemplary implantable medical device (IMD) 10. The IMD 10 includes a pulse generator 12 and a cardiac lead 14. The cardiac lead 14 operates to convey electrical signals between the heart 8 and the pulse generator 12. The proximal end 18 of the cardiac lead 14 is coupled to the pulse generator 12, and the distal end 20 of the cardiac lead 14 is coupled to the heart 8. The cardiac lead 14 includes a lead body 21 extending from the proximal end 18 to the distal end 20. The cardiac lead 14 can comprise a brady lead, a tachy lead, a heart failure lead, a pulmonary artery lead, a left side lead implantable in the left atrium and/or the left ventricle, a right side lead implantable in the right atrium and/or the right ventricle, or any other lead as is known in the art.

The heart 8 comprises a myocardium or cardiac muscle 16, a right atrium 22, a right ventricle 24, and a pulmonary artery 26. A tricuspid or atrioventricular valve 28, located between the right atrium 22 and the right ventricle 24, controls blood flow from the right atrium 22 to the right ventricle 24. A pulmonary valve 30, located between the right ventricle 24 and the pulmonary artery 26, controls blood flow from the right ventricle 24 to the pulmonary artery 26. The heart 8 further comprises a left atrium 32, a left ventricle 34, and an aorta 36. A mitral or atrioventricular valve 38, located between the left atrium 32 and the left ventricle 34, controls blood flow from the left atrium 32 to the left ventricle 34. An aortic valve 40, located between the left ventricle 34 and the aorta 36, controls blood flow from the left ventricle 34 to the aorta 36.

FIG. 1 depicts embodiments of the invention wherein the distal end 20 of the cardiac lead 14 is implanted in the right ventricle 24 and a tip electrode 41 of the lead 14 is attached to the endocardium or inner layer 46 of the heart 8. The electrode 41 may both sense electrical signals of the heart 8 and deliver electrical pulses to the heart 8 in an attempt to correct an arrhythmia and restore sinus rhythm. In other embodiments, the cardiac lead 14 may be implanted or placed within any chamber of the heart 8, as is well known in the art. For example, the distal end 20 of the cardiac lead 14 may be implanted in the right atrium 22 or the left ventricle 34 or the left atrium 32. In other embodiments, the lead is an epicardial lead and the electrode is attached to the epicardium 44, for example the epicardium 44 of the right ventricle 24, the right atrium 22, the left ventricle 34 or the left atrium 32. In such cases, the epicardial or endovascular lead can be delivered through the circulatory system of the heart to the location of interest or the epicardial lead can be delivered into the pericardial space and implanted into or onto the epicardium. In alternative embodiments, the electrode 41 may be implanted through the epicardium 44 or endocardium 46 and into the myocardium 16. In other embodiments of the present invention, the IMD 10 may include a plurality of cardiac leads 14, each with their distal end 20 placed in, implanted in, or attached to a different chamber, or a different part of the heart 8.

The implantable devices can be bipolar or unipolar. In a unipolar system, an electrode (e.g., tip electrode 41) acts as one pole of an electrical system, and the second pole of the electrical system can be located remotely from the electrode. For example, the second pole of the electrical system can be located on the pulse generator 12, or it can be located in another portion of the patient's body or on the surface of the patient's body. Various other configurations for unipolar devices are known in the art.

In a bipolar system, the implantable device can have two electrodes disposed near the site of treatment. For example, as shown in FIG. 1, a second electrode 42 can be disposed along the lead body distal portion 20. This second electrode 42 can be, for example, a ring electrode. The two electrodes 41, 42 can act as the two electrical poles of the implantable medical device 10. Various other configurations for bipolar electrodes are known in the art.

When the implantable medical device 10 is energized, an electrical potential can be created between the two electrical poles of the device 10. This potential can create an electrical field and, in some cases, can create a current between the poles. When this electrical field or current is sufficiently strong, and when myocardial cells are disposed within the field or current, the myocardial cells can become depolarized. This depolarization leads to the contraction of the heart muscle. In addition, myocardial cells have the ability to propagate this electrical signal, causing depolarization of adjacent myocardial cells. This self propagation within the myocardium allows a target area of the heart (e.g., the area of the heart corresponding to the right atrium, the right ventricle, the left atrium and/or the left ventricle) to contract upon stimulation of only a portion of the target area.

In the alternative, or in addition to stimulating the cardiac tissues, in some embodiments the electrodes of this invention can be configured to sense certain physiological attributes of the heart. For example, the heart's indigenous electrical signals can be received by an electrode and transmitted to a remote location (e.g., a pulse generator or a remote module in a leadless system). In addition, other sensing mechanisms that are known in the art can be placed on or near the electrodes, for example pressure sensors or acoustic sensors.

Figure 2:
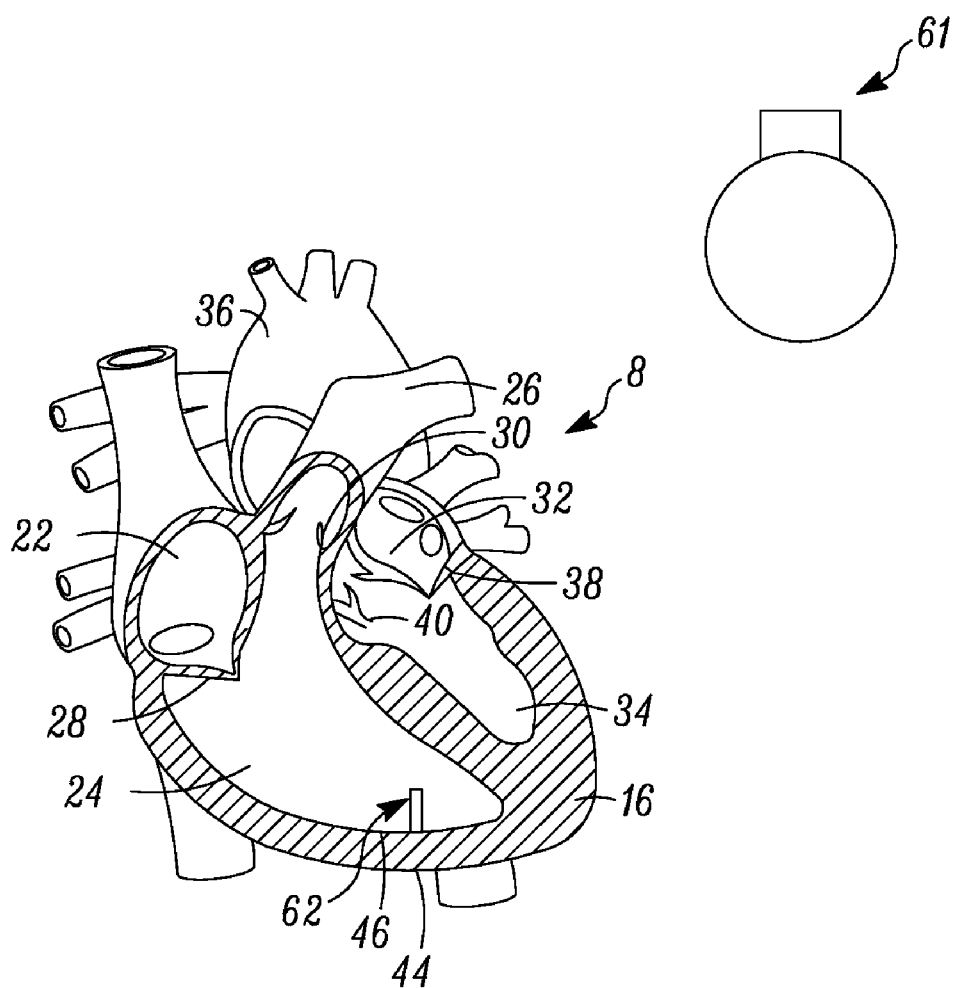
FIG. 2 shows an exemplary leadless implantable medical device according to embodiments of the present invention.

Implantable medical devices can also be configured as wireless systems, as shown in FIG. 2. Such wireless, or leadless, systems can have a remote module 61 that can be located inside or outside of a patient's body. In some cases, the remote module 61 can control the function of the microstimulator 62. The microstimulator 62 can be implantable on the endocardium, on the epicardium, or in the myocardium, for example at any of the locations mentioned with respect to the lead-based implantable medical device 10 shown in FIG. 1. The microstimulator 62 can also have one or more electrodes, for example one or more electrodes similar to those described with respect to FIG. 1.

Further, the microstimulator 62 can also have sensing capabilities as described above with respect to FIG. 1. The physiological attributes that are sensed by the microstimulator 62 can be sent to the remote module 61. Other configurations of a leadless, or wireless, implantable medical device can be found in U.S. Pat. No. 3,835,864 to Rasor et al. and U.S. Pat. No. 4,256,115 to Bilitch, both of which are incorporated by reference in their entirety.

FIG. 3A shows a perspective view of a portion of an example implantable medical device according to embodiments of the invention. In this example, the implantable medical device has a pair of electrically isolated electrodes 70, 71 disposed in close proximity to one another. As shown, the electrodes 70, 71 can be disposed on a tip 79 of an implantable medical device. The tip 79 can be disposed at the implantable end of device body 200. The device body 200 can be any structure that carries electrodes in implantable devices, for example a lead or the body of a microstimulator. As examples, the device body 200 can be the lead body 21 (shown in FIG. 1) or the body of the microstimulator 62 (shown in FIG. 2).

In various embodiments, the tip 79 may also include a fixation system (not shown) disposed on the tip to fix the device at a desired location. Any fixation structures known in the art may be used.

Turning to FIG. 3B, each of the electrodes 70, 71 can comprise a support 72, 73 and a nanostructure coating or array 74, 75 disposed on the supports 72, 73. The nanostructure coating 74, 75 can cover at least a portion, or the entire, outer working surface of the supports 72, 73. The nanostructure coating may be deposited (i.e., grown) onto the supports 72, 73 using any of a variety of techniques known in the art, as mentioned further below.

In some cases, the supports 72, 73 are part of the electrical pathway used to transmit electrical energy to or from the nanostructure coatings 74, 75. In such a case, the supports 72, 73 can be electrically isolated from one another in order to prevent the electrical energy from shorting between the supports 72, 73 rather than being communicated to or from the nanostructure coatings 74, 75. In order to prevent such shorting of an electrical signal, the supports 72, 73 can be electrically isolated from one another along interface 76. As an example, the supports 72, 73 could be separated by an insulative material. In other embodiments, the supports 72, 73 are formed from a conductive portion of the lead body (e.g., a conductive polymer).

Further, the device body 200 can comprise insulative material or the supports 72, 73 can be insulated from the device body 200, for example by an insulative material being placed along the interfaces 77, 78 between the supports 72, 73 and the device body 200. This can prevent an electrical signal from shorting between the supports 72, 73 by traveling through the device body 200.

As shown in FIG. 3B, the supports 72, 73 can be attached to and form a tip portion of the device body 200. In other cases, the supports 72, 73 can be disposed over a tip portion of the device body 200. In embodiments where the supports 72, 73 are formed over a portion of the device body 200 and the device body 200 is conductive, an insulative barrier can be placed between the inner surface of the supports 72, 73 and the outer surface of the device body 200 on which the supports 72, 73 are disposed. Again, this can prevent electrical energy from shorting between the supports 72, 73 through the device body 200.

The implantable device can further comprise electrical connections 201, 202 as shown in FIG. 3B. The electrical connections 201, 202 can be electrically coupled to the electrodes 70, 71. For example, the electrical connections 201, 202 can be electrically coupled to the electrode supports 72, 73 at coupling points 203, 204. The electrical connections 201, 202 can also be coupled to a source of electrical energy, for example a pulse generator. This can allow electrical energy to be transmitted from the source of electrical energy, through the electrical connections 201, 202 to the electrodes 70, 71. For example, the electrical energy can be transmitted through the electrical connections 201, 202 to the electrically conductive supports 72, 73 and to the nanostructure coatings 74, 75. The connections 201, 202 may be of any type known in the art, for example cable or coil conductors.

As shown in FIG. 3B, the device body 200 can define a lumen 205. In some cases, the lumen 205 can extend from near the tip 79 of the device proximally to a proximal end of the device. In other cases, the lumen 205 can extend from near the tip 79 of the device proximally to an electrical pulse generation source. Although FIG. 3B is shown with a closed tip 79, the tip 79 can also have an opening communicating with the lumen 205. The electrical connections 201, 202 can extend through all or a portion of the lumen 205.

In FIG. 3B, the device body 200 is shown with a single lumen 205. In other embodiments, the device body 200 can have multiple lumens. For example, the device body 200 can have a first lumen with electrical connections (e.g., 201, 202) extending down the first lumen and a second lumen, for example a second lumen that can accommodate a stylet. It is also noted that the device body 200 could instead be solid along at least a portion of the device body 200, and electrical connections can be disposed within the solid device body 200.

When electrical energy is supplied to the nanostructure coatings 74, 75, an electrical field can be created between the nanostructure coatings 74, 75 and in some cases an electrical current can flow between the nanostructure coatings 74, 75. The nanostructure coatings 74, 75 can be incorporated into the electrodes as further discussed below with respect to FIGS. 6A-7B.

In various embodiments, the insulative barriers (e.g., 76, 77, 78) that can be present in order to prevent possible shorting of the electrical energy between the supports 72, 73 can also form an electrical barrier isolating the nanostructure coatings 74, 75. Alternatively, additional insulative coating materials can be placed between the nanostructure coatings 74, 75 in order to electrically space the nanostructure coatings 74, 75 apart from one another, or the nanostructure coatings 74, 75 could be formed with a space between them. Further, it is also contemplated that the nanostructure coatings 74, 75 can comprise a single nanostructure coating that is formed over both electrode supports 72, 73.

FIG. 4A and 4B depict an additional exemplary embodiment wherein the electrodes are disposed on a portion of the implantable medical device other than the tip 79. As shown in this Figure, the electrodes 80, 81 can be disposed along a portion of the device body 200. In some cases (as shown in FIG. 4A) the pair of electrodes 80, 81 can be disposed near the tip 79 of the device body 200.

In some embodiments, the pair of electrodes 80, 81 can be located in close proximity to the tip 79. For example, in lead configurations intended for use in a coronary vein, the electrodes 80, 81 can be located 1-3 cm away from the fixation site (e.g., the fixation site can be at or near the tip 79 as mentioned above). In addition, multiple pairings of electrodes can be disposed along the device body 200, as further discussed below with respect to FIG. 5.

Turning to FIG. 4B, the electrodes 80, 81 can each comprise a support 82, 83 and a nanostructure coating 84, 85 disposed over the supports 82, 83. In the example of FIG. 4B, the supports 82, 83 can be ring shaped supports. Although the supports 82, 83 are shown as essentially forming a part of a wall of a tubular device body 200, other configurations are also possible. For example, the supports 82, 83 could be shaped like rings or other shapes and disposed over a portion of the device body 200 at a desired location. The device body 200 can have any of the designs mentioned above with respect to FIGS. 3A and 3B.

Similar to the embodiment described with respect to FIGS. 3A and 3B, the embodiment shown in FIGS. 4A and 4B can have insulative portions in order to prevent possible shorting of electrical energy between the supports 82, 83. These insulative portions are shown at 86 (this portion can insulate the two supports 82, 83 from one another) and at 87 and 88 (these two portions can insulate the supports from the remainder of the device body 200). Further, an insulative structure could also be formed between the inside surface of the supports 82, 83 and an outside portion of the device body 200 in those embodiments where the supports 82, 83 are disposed over a portion of the device body 200.

The nanostructure coatings 84, 85 can also have insulation or spacing between them, as mentioned above with respect to FIG. 3B, or the coatings 84, 85 can be formed as a single nanostructure coating over the two supports 82, 83. Also shown in FIG. 4B are connections 201, 202 and coupling points 203, 204, which are further described above with respect to FIG. 3B.

In some embodiments, during operation of the implantable medical device, one polarity of electrical energy is delivered through one of the connections 201, 202 and another polarity of electrical energy is delivered through the other connection 201, 202. For example, the connections 201, 202 can each be attached to opposing poles of an electrical circuit. As such, the nanostructure coatings will have opposing electrical potentials. Because of these opposing electrical potentials, an electrical field (and possibly an electrical current) can be established between the nanostructure coatings.

In other embodiments, the devices can be used in a unipolar configuration. One or more electrodes (e.g., any of the electrodes described herein) can be disposed on the device and one connection can be coupled to the one or more electrodes. These one or more electrodes can form the first pole of an electrical circuit. Another pole of an electrical circuit can then be disposed at a location remote from the one or more electrodes. When electrical energy of opposing polarities is supplied to the one or more electrodes and the remote pole, an electrical potential can be formed between the two locations, establishing an electrical field (and possibly an electrical current). In some cases, a device can have multiple electrodes that are each electrically attached to a separate connection. In such a case, the electrodes can be electrically activated at different times and/or the electrode with the lowest threshold potential can detected and used.

Figure 5:
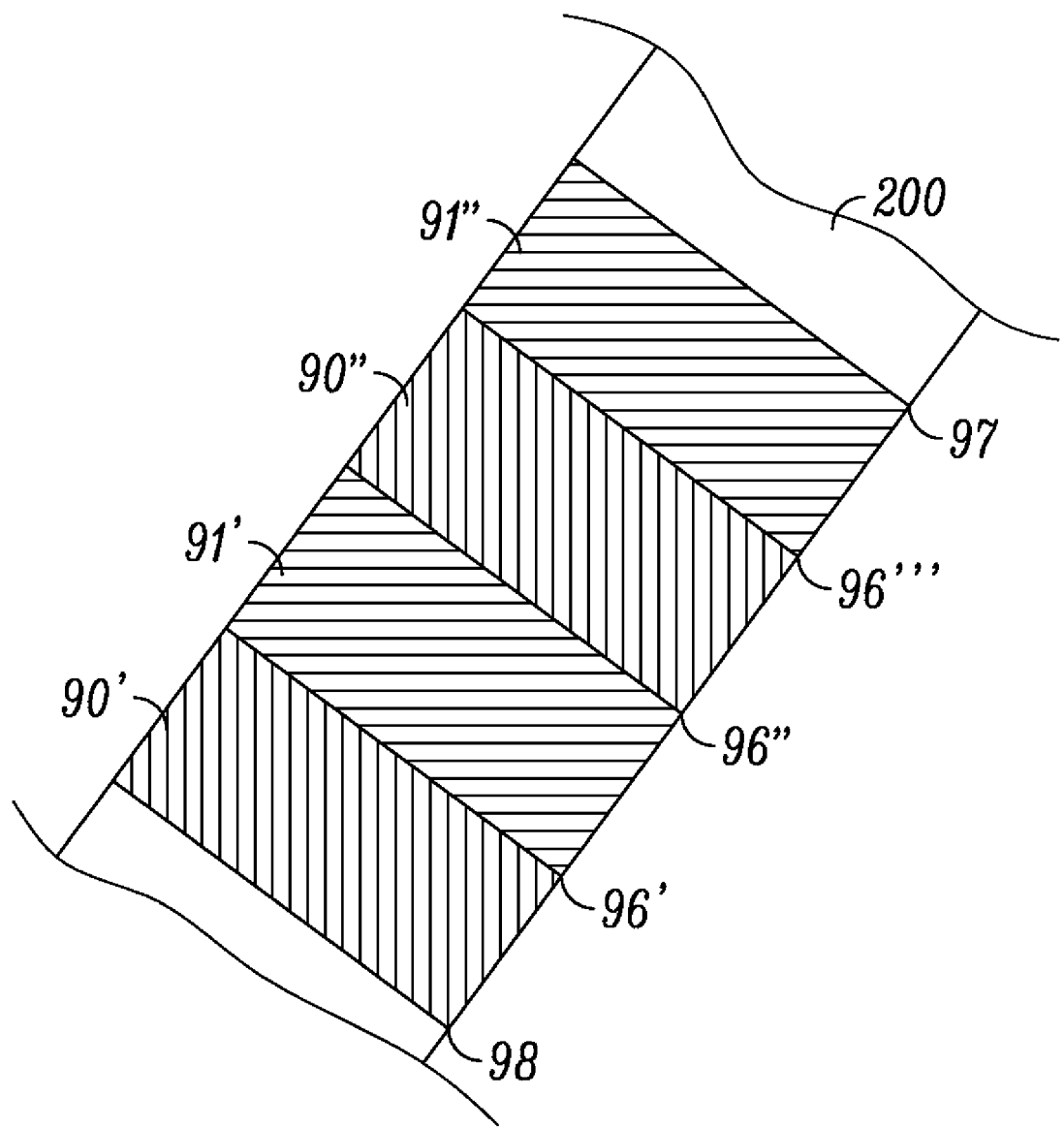
FIG. 5 shows a perspective view of an array of electrodes according to embodiments of the present invention.

Further, as shown in FIG. 5, in some embodiments an implantable medical device can have more than two electrodes. In some cases, the more than two electrodes can be formed in an array of electrodes. The array of electrodes can have pairs of electrodes (e.g., 90' paired with 91' and 90" paired with 91"). The pairs of electrodes can be similar to the pairs of electrodes described with respect to FIGS. 3A-4B above. Supports for the electrodes can be electrically separated from one another by insulative portions 96', 96", 96''' and supports for the electrodes can be electrically separated from the device body 200 by insulative portions 97, 98. In some embodiments, the pairs of electrodes can be spaced apart along the device body 200.

In some embodiments, each of the first electrodes in the pairs of electrodes can be electrically coupled to the same first connection and each of the second electrodes can be electrically coupled to the same second connection. In this case, all of the pairs of electrodes will be electrically energized at the same time. This can allow for near simultaneous stimulation of multiple tissue locations.

In other embodiments, each of the electrodes can be electrically coupled to a separate connection. In such a case, each pairing of electrodes can be electrically activated at different times. For example, the electrodes can be selectively activated depending on which has the lowest stimulation threshold voltage. In other examples, different pairings of electrodes can be activated at different times, allowing for sequential stimulation of different areas of tissue. This sequential activation of different pairings of electrodes can propagate up or down the device body 200 or in any other desired sequence.

Figure 6A:
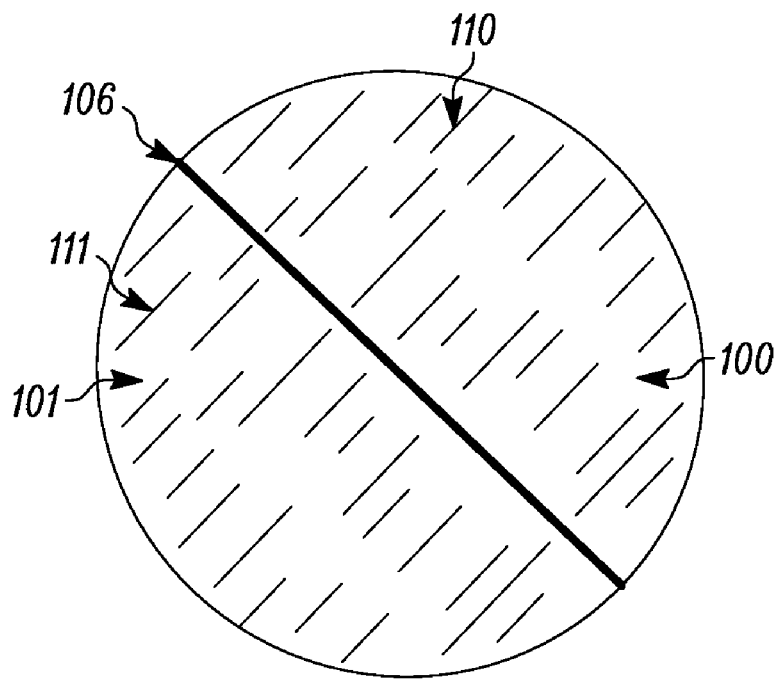
FIGS. 6A and 6B show magnified views of a pair of electrodes according to embodiments of the present invention.

Turning to FIG. 6A, a magnified view of the interface 106 between two electrodes 100, 101 is shown. These electrodes 100, 101 can be any of the electrode pairs disclosed herein, with the interface 106 being any of the insulative barriers described herein (e.g., 76, 86, 96', 96", 96'''). The electrodes 100, 101 can each comprise nanostructures (e.g., 110, 111).

The nanostructures can be either electrically conductive (i.e., metallic), semiconductive or insulative (e.g., an oxide). The nanostructures can be nanotubes (single walled or multiple walled), nanowiskers, nanowires, nanoparticles, a nanotextured surface, a nanomesh, or the surface can have a nanotopography, or any other nanostructure known in the art can be used. In FIG. 6A, the nanostructures are shown as elongated nanostructures, for example nanotubes, nanowhiskers or nanowires. In some embodiments, the nanostructures can have at least one dimension that is between 0.1 and 100 nm.

As is known in the art, nanostructures can comprise a variety of materials. For example, nanostructures can comprise carbon, silicon, boron, copper gold, silicon dioxide, polycaprolactone (e.g., a nanofibrous polycaprolactone mesh) or polyethylene glycol. Further, as is known in the art, nanostructure materials can be doped with different materials in order to change their properties. For example, certain nanostructure materials can be doped in order to make them more electrically conductive.

As shown in FIG. 6A, the elongated nanostructures 110, 111 can be oriented in a pattern in which the nanostructures are generally aligned with one another. In exemplary embodiments, the pattern can further be aligned with a longitudinal axis of the device body. Nanostructures can also be arranged in a grid with an approximately 200 nm spacing such as that described by Kim et al., "Modulation of Adhesion and Growth of Cardiac Myocytes by Surface Nanotopography," Proceedings of the $27^{th}$ Annual International Conference of the IEEE Engineering in Medicine and Biology Society, Shanghai, China, Sep. 4, 2005, which is herein incorporated by reference in its entirety. The nanostructures can also be arranged to form a nanomesh, as described in Shin et al., "Contractile cardiac grafts using a novel nanofibrous mesh," *Biomaterials*, Volume 25, Issue 17, August 2004, pages 3717-3723, which is incorporated herein by reference. In other embodiments, the nanostructures 110, 111 can be oriented in a random pattern or any other pattern.

In some cases, aligning the elongated nanostructures 110, 111 can result in more effective electrical interaction between the nanostructures 110, 111 between electrodes (e.g., stronger electrical fields or currents can be generated with a given applied voltage). The distance between the nanostructures 110, 111 at the interface 106) of the electrodes 100, 101 can also affect the strength of the electrical field or current. This distance (which is further discussed below) can be governed in some cases by the spacing between the nanostructure coatings. Further, if an insulative coating is disposed between the nanostructure coatings, this insulative coating can also affect the strength of the electrical field or current.

The nanostructures can be disposed on the supports or on any other desired structure using a variety of methods known in the art. Some of the possible methods for nanostructure deposition are described in U.S. Pat. No. 7,162,308 entitled "Nanotube Coatings for Implantable Electrodes", U.S. Patent Publication 2006/0239891 entitled "Methods of Oxidizing Multiwalled Carbon Nanotubes", U.S. Patent Publication 2004/0111141 entitled "Medical Devices Incorporating Carbon Nanotube Material and Methods of Fabricating the Same", and U.S. Pat. No. 7,079,903 entitled "Low Polarization Coatings for Implantable Electrodes". All of these patents and publications are herein incorporated by reference in their entirety. These references also mention a variety of materials that can be used for the supports, including tantalum, zirconium, platinum, iridium, and niobium, among others.

Figure 6B:
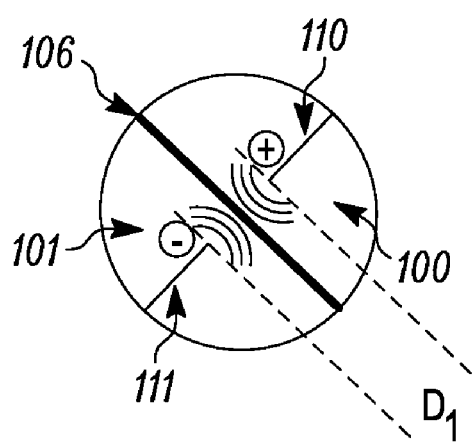

As an example, as shown in FIG. 6B, when the electrodes 100, 101 are supplied with electrical energy, the electrical energy is communicated to the nanostructures 110, 111. When the nanostructures 110, 111 have opposite electrical polarities, an electric field (and, in some cases, a current) can be established between two individual nanostructures on opposing electrodes (e.g., see the lines between nanostructures 110, 111 in FIG. 6B). In general, the close proximity of the nanostructures 110, 111 (indicated by the distance $D_1$) can allow for a relatively strong localized electrical field (and possibly electric current) to be established with a relatively low voltage potential between the electrodes. As mentioned above, stimulation of myocells within this relatively small electrical field can be propagated through a larger area of the heart via the propagation mechanism of the heart's myocardium.

Cells (e.g., myocardial cells, myocardial progenitor cells, neural cells, or stem cells) can be disposed within the electrical field or current in a variety of ways. In some embodiments, the electrodes 100, 101 can be implanted in the body, and cells can be disposed in the electrical field due to the location and orientation of implantation of the electrodes 100, 101.

In other exemplary embodiments, cells can be deposited in vivo or in vitro on the device, and as a result some cells can be deposited and/or grow within the area in which the electrical field or current will be established. Cells can be disposed on the device between the nanostructures 110, 111, for example on the electrode supports or on an insulative material that may be placed between the electrodes. In such cases, the surfaces on which the cells are to be disposed can be physically conditioned (e.g., provide a roughened surface) or pharmacologically treated (dispose cell-growth promoting drugs and/or cell growth factors on the surfaces) in order to promote cell growth on those surfaces. In some examples, cells can be deposited in vitro on the device, and when placed in the body additional cells can be deposited on the device in vivo. In such an embodiment, the types of cells that are initially placed (as well as the location and manner of placement) can be closely controlled in vitro, which can encourage desirable cell growth once the device is implanted in the human body and/or discourage fibrotic growth on the electrode.

Further, if the type of cells deposited in vitro are myocells, upon implantation the deposited myocells can, when stimulated, propagate the stimulation to indigenous myocells, causing stimulation of the target area of heart tissue.

In some embodiments, the spacing of the nanostructures 110, 111 can be sufficiently close to allow for a strong electrical field to be established but spaced sufficiently far apart to allow for a high probability that cells will be disposed between the nanostructures 110, 111. As an example, the electrodes (and/or the nanostructure coatings) can be spaced apart (e.g., spaced apart along interface 106) approximately one times the diameter of a single cardiac myocyte (i.e., approximately 15 μm). In some cases, the spacing can be about twice the diameter of a single myocyte (i.e., approximately 30 μm), about three times the diameter of a single myocyte (i.e., approximately 45 μm), or about five times the diameter of a single myocyte (i.e., approximately 75 μm). In other embodiments, the spacing can be less than five times the diameter of a single cardiac myocyte (i.e., less than approximately 75 μm), less than three times the diameter of a single cardiac myocyte (i.e., less than approximately 45 μm), less than two times the diameter of a single myocyte (i.e., less than approximately 30 μm) or less than the diameter of a single myocyte (i.e., less than approximately 15 μm).

Figure 7A:
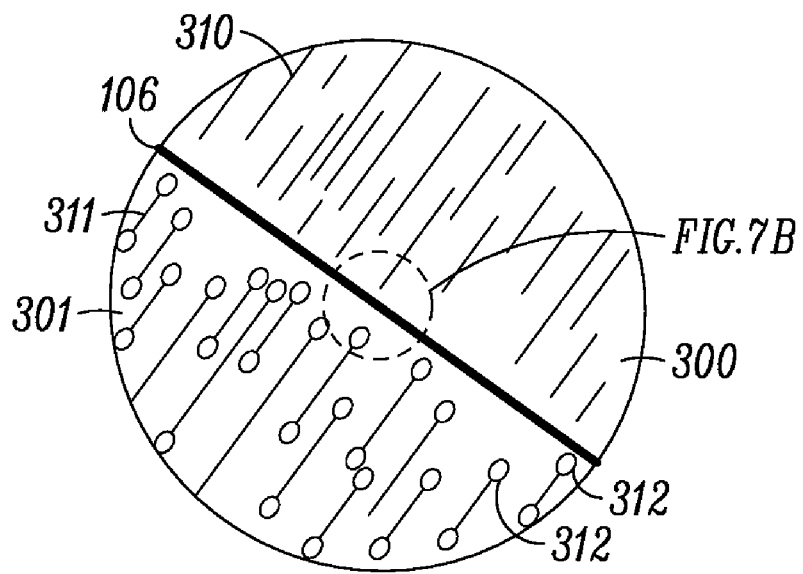
FIGS. 7A and 7B show magnified views of a pair of electrodes according to embodiments of the present invention.
Figure 7B:
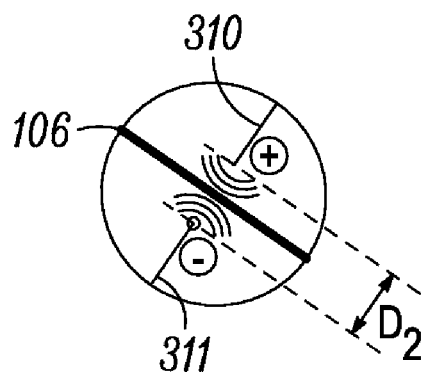

Turning now to FIGS. 7A and 7B, an alternate embodiment shows a pair of electrodes 300, 301 with elongate nanostructures 310, 311. As an alternative to elongate nanostructures disposed in an aligned orientation, the nanostructures 310, 311 can be any of the nanostructures discussed with respect to FIGS. 6A and 6B, and can be disposed in any of the orientations discussed with respect to FIGS. 6A and 6B. In FIGS. 7A and 7B, cells 312 are disposed on the nanostructures 310, 311. Shown in these Figures are cells disposed on the ends of the elongate nanostructures; however, the cells can also be disposed on other portions of the elongate nanostructures. Having cells disposed on the nanostructures 310, 311 can increase the likelihood that cells are located within any electrical field or current that is created between the nanostructures 310, 311.

As shown in FIGS. 7A and 7B, cells 312 can be disposed on the nanostructures 311 of one of the electrodes 301, but the nanostructures 310 of the other electrode 300 can have fewer cells (i.e., no cells) than the nanostructures 311. In some cases, the nanostructures 311 can have fewer cells than nanostructures 311 (e.g. no cells) before implantation of the electrodes. Further, the nanostructures and/or the entire electrode 300 can be treated to prevent cell growth after implantation. In another embodiment, the nanostructures 310, 311 of both electrodes 300, 301 can have cells disposed thereon.

In some cases, the cells can be deposited on the nanostructures 310, 311 before the nanostructures 310, 311 are incorporated into the electrode 300, 301 and in other cases the cells can be deposited on the nanostructures 310, 311 after the nanostructures 310, 311 are incorporated into the electrode 300, 301.

Depositing cells on one or both of the nanostructures 310, 311 in vitro may have a variety of benefits. In some cases, the in vitro cells can instigate a less intense (e.g., no) immune response in the body compared to the immune response instigated by nanostructures with no cells disposed on them. This can have several benefits, including the prevention of fibrotic growth on the electrode surface (fibrotic growth can result in a higher required voltage to stimulate or sense cells). Different tissue reactions are described in Mase et al., "Histopathological Study or Tissue Reaction to Pacemaker Electrodes Implanted in the Endocardium," *Journal of Nippon Medical School*, volume 72, No. 1, pages 52-59 (2005), which is herein incorporated by reference in its entirety. In some cases, the presence of cells before implantation may also facilitate the deposition of the desired type(s) of cells, and facilitate the deposition of the cells in the desired manner (location, pattern, etc). As an example, cardiac myocytes can be deposited in vitro on one or both of the nanostructures 310, 311. When these cardiac myocytes are implanted within a human body, the growth of other cardiac myocytes may be encouraged by the presence of the in vitro cardiac myocytes.

As shown in FIG. 7B, the distance $D_2$ is the distance between nanostructures 310, 311. As mentioned above with respect to FIG. 6B, this distance can be the width of the interface 106. In other words, if the nanostructure coatings of the electrodes 300, 301 are separated by the interface 106 and the interface has a width, increasing this width can, all else being equal, decrease the strength of the electrical field or current that is formed between the nanostructure coatings. Again, the spacing between the electrodes (and/or the spacing between the nanostructure coatings) can be any of the dimensions mentioned above with respect to FIG. 6B.

In another embodiment, a method of coating nanostructures with cells is disclosed. Nanostructures can be produced and placed in a solution. For example, nanostructures that are disposed on a support can be placed in the solution by placing the support in the solution. The type of cells that are desired to be coated on the nanostructures can also be placed in the solution. If the nanostructures have a compatible chemistry (discussed below), then the cells will settle onto and gradually incorporate the nanostructures into the cells.

In order to promote the incorporation of the nanostructures into the cells, the nanostructures can have a chemical composition that makes the nanostructures compatible with cell membranes. This can facilitate the growth of the cell membranes around the nanostructures and can also facilitate longer cell life. As one example of a biocompatible chemical composition, the nanostructures can comprise silicon and at least a part of the nanostructures can comprise silicon dioxide. The silicon dioxide can provide a biocompatible surface on which cells can settle. Further, due to the biocompatibility of the silicon dioxide, the cells can incorporate the nanostructures into the cells. In some examples, the size of the nanostructure can also affect a cell's ability to successfully incorporate or encapsulate the nanostructure. For example, nanostructures (i.e., nanotubes) with at least one dimension (i.e., a diameter of the nanotubes) of less than 90 nm, or from 30-90 nm, can enhance cell longevity compared to larger dimensions such as 400 nm.

In addition, as mentioned above, a nanofibrous polycaprolactone mesh or polyethylene glycol can be used as a substrate in which to grow cardiomyocytes. In some cases, polycaprolactone and polyethylene glycol nanostructures may be biocompatible and may also promote cell growth or in-growth as discussed above with respect to silicon dioxide nanostructures.

In various embodiments, the source of cells for the cell deposition can include at least one of autologous, isologous, allogeneic, or xenogeneic cells. In some cases, autologous cells can eliminate or reduce cell rejection. However, in patients too ill or suffering from chronic conditions, cell harvesting can be undesirable. Non-autologous cells may be used in such cases. The use of non-autologous cells can also provide an additional benefit of allowing devices to be prepared before a specific patient is identified, which can reduce any delay from the time the patient is identified to the time of implantation.

In other embodiments of the invention, any of the electrode systems mentioned herein can be incorporated into a lead-based or leadless neural stimulation system. In some embodiments, the electrodes can be incorporated into a neural system in the same manner that electrodes are incorporated into the cardiac systems described herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cardiac medical device comprising:
   an implantable device body with an array of cardiac electrodes disposed thereon;
   the array including a plurality of electrode pairs disposed on the device body, each electrode pair including a first cardiac electrode electrically connected to a first electrical connection and having a first electrical pole, and a second cardiac electrode electrically connected to a second electrical connection and having a second electrical pole with an electrical potential different than the first electrical pole;
   the first and second electrodes comprising nanostructures that are configured to allow living cells to at least partially incorporate the nanostructures;
   wherein at least a portion of the nanostructures of the first electrodes are at least partially incorporated into the living cells; and
   wherein the electrode pairs are configured such that an electrical potential exists between the first and second electrodes of each electrode pair when the medical device is energized, and wherein the first and second electrodes of each electrode pair are spaced apart from one another via a distance between about 15 µm to about 75 µm.

2. The device of claim 1, wherein at least a portion of the nanostructures of both the first and second electrodes are at least partially incorporated into living cells.

3. The device of claim 1 wherein the nanostructures are at least partially incorporated into cells at least partially in vitro.

4. The device of claim 2 wherein the nanostructures are at least partially incorporated into cells at least partially in vitro.

5. The device of claim 1 wherein the cells are selected from a group consisting of myocardial cells, myocardial progenitor cells, neural cells and stem cells.

6. The device of claim 1, wherein the nanostructures of the first and second electrodes are substantially oriented in a longitudinal direction along a support.

7. The device of claim 1, wherein the nanostructures of the first and second electrodes are disposed on a support in a substantially random fashion.

8. The device of claim 1, wherein the nanostructures of the first and second electrodes are disposed on a support surface in a substantially two dimensional grid.

9. The device of claim 1, wherein each of the first electrodes is electrically connected to a separate first electrical connection and each of the second electrodes is electrically connected to a separate second electrical connection.

10. The device of claim 1, wherein the first electrodes are electrically connected to a common first electrical connection and the second electrodes are electrically connected to a common second electrical connection.

11. The device of claim 1, wherein the device body comprises a lead of a cardiac medical device.

12. The device of claim 1, wherein the device body comprises a microstimulator of a leadless cardiac rhythm management device.

13. The device of claim 1, wherein the nanostructures are selected from a group consisting of nanowires, single walled nanotubes, multiple walled nanotubes, a nanotextured surface, a surface nanotopography, a nanomesh, nanoparticles and nanowiskers.

14. The device of claim 1, wherein each pair is spaced apart from one another less than approximately the diameter of one myocyte.

15. A bipolar cardiac medical electrical lead comprising:
    a first implantable cardiac electrode electrically connected to a first electrical connection and having a first electrical pole, and a second implantable cardiac electrode electrically connected to a second electrical connection and having a second electrical pole with an electrical potential different than the first electrical pole, wherein the first and second electrodes are configured such than an electrical potential exists between a lead interface of the first and second electrodes when at least one of the first and second electrodes is energized;
    the first and second electrodes comprising first and second supports with first and second nanostructure coatings disposed on the first and second supports, respectively;
    the nanostructure coatings of the first and second electrodes being spaced apart from one another such that at least one of the first nanostructures of the first nanostructure coating and at least one of the second nanostructures of the second nanostructure coating are spaced apart, the space between the at least one of the first nanostructures of the first nanostructure coating and the at least one of the second nanostructures of the second nanostructure coating being less than approximately 45 µm from one another.

16. The lead of claim 15 wherein at least a portion of the nanostructures of the first electrode is incorporated into living cells.

17. The lead of claim 15 wherein at least a portion of the nanostructures of the first and second electrodes are incorporated into living cells.

18. The lead of claim 16 wherein the nanostructures are at least partially incorporated into living cells at least partially in vitro.

19. The lead of claim 17 wherein the nanostructures are at least partially incorporated into living cells at least partially in vitro.

20. The lead of claim 18 wherein the cells are selected from a group consisting of myocardial cells, myocardial progenitor cells, neural cells and stem cells.

21. The lead of claim 15 wherein the nanostructures of the first and second electrodes are oriented in a longitudinal direction along the support.

22. The lead of claim 15, wherein the nanostructures of the first and second electrodes are disposed on the support in a substantially random fashion.

23. The lead of claim 15, wherein the nanostructures of the first and second electrodes are disposed on the support surface in a substantially two dimensional grid.

24. The lead of claim 15, wherein the nanostructures are selected from a group consisting of nanowires, single walled nanotubes, multiple walled nanotubes, a nanotextured surface, a surface nanotopography, a nanomesh, nanoparticles and nanowiskers.

* * * * *